United States Patent [19]
Carr et al.

[11] Patent Number: 5,080,807
[45] Date of Patent: Jan. 14, 1992

[54] CONTINUOUS PARTICLE SEPARATION PROCESS

[75] Inventors: Charles Carr, Edgewater; Edward Sybert, Rockville; Aldis E. Adamson, Columbia, all of Md.

[73] Assignees: Espro, Columbia; The University of Maryland, College Park, College Park, both of Md.

[21] Appl. No.: 639,276

[22] Filed: Jan. 10, 1991

[51] Int. Cl.$^5$ .................. B01D 33/41; B01D 33/54; B01D 37/00; B01D 21/26

[52] U.S. Cl. ....................... 210/772; 209/2; 209/17; 209/269; 210/651; 210/779; 210/781; 210/785; 210/805; 210/806; 436/177

[58] Field of Search ............ 210/651, 772, 779, 781, 210/785, 805, 806; 209/2, 17, 235, 250, 269, 311; 436/177, 178; 424/93

[56] References Cited

U.S. PATENT DOCUMENTS

| | | | |
|---|---|---|---|
| 4,186,195 | 1/1980 | Yearian | 424/93 |
| 4,427,551 | 1/1984 | Duveau | 210/805 |
| 4,716,039 | 12/1987 | Rogoff et al. | 424/93 |
| 4,871,462 | 10/1989 | Fischel et al. | 210/651 |
| 4,879,048 | 11/1989 | Kreyenberg | 210/806 |

Primary Examiner—W. Gary Jones
Attorney, Agent, or Firm—Oblon, Spivak, McClelland, Maier & Neustadt

[57] ABSTRACT

A continuous process for the separation of small particles from larger particles in a biological preparation passes a liquid stream of the preparation through a first filter or screen, which retains larger particles, passing smaller particles in the liquid. The large particles have retained on their surfaces wetting water, in which are entrained some of the small particles. The large particles are directed to a liquid having a concentration of smaller particles lower than the concentration of smaller particles in the wetting water, and mixed therein. The smaller particles separate from the larger particles in the mixed suspension, which is then directed to a second filter or screen, for further separation. The smaller particle/liquid stream may be recycled to the biological preparation stage, the liquid suspension for the large particles, or to a separator means where the smaller particles are separated off from the liquid stream. As the system is susceptible of being practiced as a continuous closed system, given an adequate liquid supply, the filtering steps may be repeated any number of times. When separated at the filters or screens, at least a portion of the stream of small particles and liquid must be directed to the separation means, so that said small particles may be eventually separated.

7 Claims, 1 Drawing Sheet

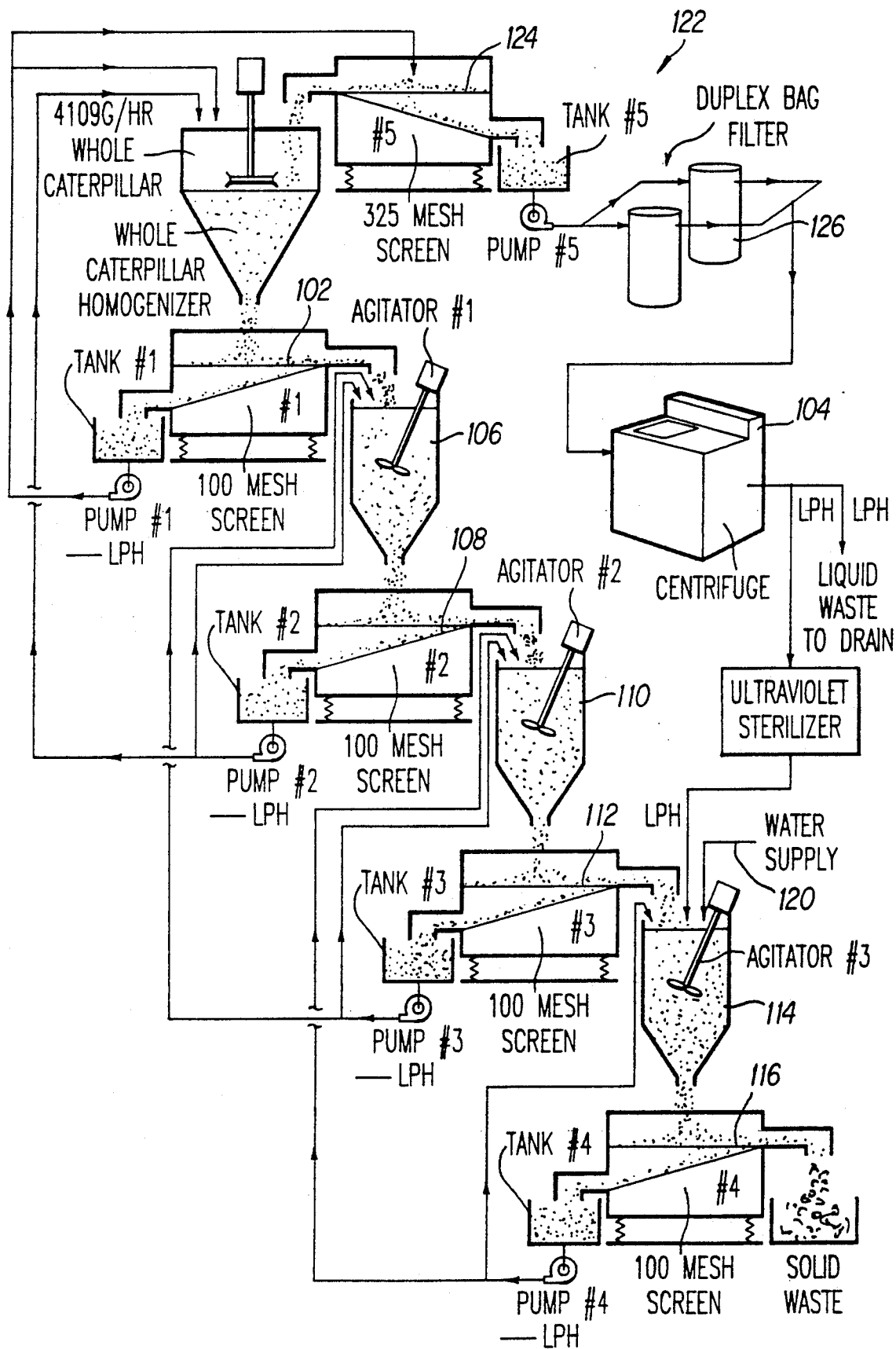

CONTINUOUS PARTICLE SEPARATION PROCESS

BACKGROUND OF THE INVENTION

1. Field of the Invention

The invention involves a continuous process for separation of particles of a given size range from a preparation containing solid particles having a wide size distribution range. By way of example, small, heavy particles from biological preparations, such as tissue homogenates, can be easily separated from the larger particles associated with the biological debris present. Particles on the order of 1–2 microns and the like, such as inclusion bodies and like, which may contain or constitute, valuable biological materials, can be easily recovered in a substantially concentrated form. Inorganic materials over a given size distribution can be similarly separated in concentrated form.

2. Background of the Prior Art

For some time, it has been recognized that it is frequently desirable to concentrate specific particles from a biological preparation, which particles may contain or be valuable biological materials. Thus, it is known that various pesticides and similar agricultural treatments, can be prepared from viruses and other biological agents obtained from the insects sought to be regulated, rather than from artificial, and potentially hazardous, chemicals. One example is the natural virus pesticide being used to control the devastation raked by the gypsy moth in the northeastern United States, exemplified by the virus-based pesticide useful in controlling that moth, prepared from the nuclearpolyhedrosis virus that infects that species. In general, these viruses and similar biological agents, can be obtained from, inclusion bodies and similar small organelles or biomaterials found in the cells of the organisms in question. As an alternative embodiment, in cells prepared as expression vehicles by recombinant engineering, many valuable biological agents, such as interferon and interluken-2, are contained primarily in similar inclusion bodies. The isolation of these inclusion bodies, from other solid biological debris, remains a preliminary step to the utilization of these valuable biological agents.

Additionally, many products require effective, efficient and economical methods for increasing the concentration of particles of a given size from a raw material source. One example is the collection of clays from slurries of mined materials.

Current separation technologies are not adequate to the task of separating large and small solid particles from a liquid preparation, such as a biological homogenate without excessive coat. In general, these processes are confined to a simple separation, centrifugation and drying. Generally, this is inadequate to achieve a useful separation. This is particularly because the large solids leaving the screen, e.g., cheesecloth, carry water wetting their surfaces. Smaller sized solids will be entrained with the water. Thus, subsequent collection of large solids, followed by centrifugation, will not result in separation of the small and large particles. In the alternative, if the small particle is the desired recovery object, a substantial amount of small particle recovery will be missed, due to the retainment of those small particles in the large particle separation discussed above. Alternative, all-dry processing, fails to exclude undesirable particles from the final preparation obtained.

Accordingly, it remains an object of the industry to provide a simple, straightforward and effective method for the separation of particles, based on size discrimination, from a liquid preparation. Particular emphasis is placed on the separation of small, heavy particles, such as inclusion bodies, from larger particles of similar weight found in a biological preparation.

SUMMARY OF THE INVENTION

The above objects, and other objects made evident by the discussions set forth below, are achieved by a continuous process, employing apparatus which includes one or more recirculation pumps, at least two screens or filters separating particles of a given size and a separator or similar device for removing isolated particles from an aqueous suspension.

The preparation, such as a biological homogenate, is prepared with an excess of water. The suspension is forwarded to a first screen or filter in step (A) which separates particles by allowing particles of a given diameter and below to pass, while large particles are retained and/or removed by the filter. If isolation and ultimate use of the smaller particles is desired, the small particles/water stream may be subjected to filtration and centrifugation, to isolate the smaller particles, the supernatant from the centrifugation or filtration being used in a separate process step (B) for separation of small particles entrained in the large particle surface water, which large particles were separated off by the first screen in step (A). The recovered small particles are appropriately processed and prepared for use. The large particles separated off from the first screen in process step (A) are combined with a portion of the supernatant recovered from the small particle preparation process step (B), that portion being sufficient to provide a water suspension in which the concentration of small particles is lower than the concentration of small particles in the water entrained on the surface of the large particles separated off from the first screen. The large particles are thoroughly mixed, by, e.g., agitation, in the low-small particle-concentration water, until a uniform distribution of the large solids in the water is obtained. This preparation is forwarded to a separate screen or filter (second screen) wherein the large solids are again separated off in step (C), and the small particles, together with the water passing through the screen, are recovered, and may be forwarded either to the centrifugation or similar separator stage for process step (D), or recycled all the way back to the beginning, for further separation. Fresh preparation water or other liquid support is introduced into the final agitation step, and is thereby recycled upward through the separation steps, to provide the reduced concentration values necessary. The countercurrent flow of feed material and fresh liquid is an essential aspect of the invention.

It will be immediately apparent that the large solid particles separated off from the second screen at step (C) will have, in the wetting water retained on their surface, a lower concentration of small particles than that exhibited in the wetting water of the large particles separated off at the first screen in process step (A). The solid particles may be further resuspended, separated, the recovered small particles being returned for recycling and separation, as many times as is practical and profitable, given the material being recovered. At a minimum, the continuous process of this invention contemplates two distinct separation steps, by filter, screen, etc. Substantial economies can be obtained by thorough recycling. Thus, of the supernatant recovered from the small particle centrifugation, a portion may be used for preparation of the suspension of the large particles. The remainder may be recycled as the water supply for the biological preparation to be treated. A five-screen process is illustrated in the figure.

The system is liquid supply conservative, and contemplates the use of ordinary water supplies. However, given the liquid conservative nature of the process, other liquids, desirable as suspension mediums may be employed where necessary. It should be further noted that the process is designed as a continuous one. Although separate screens, centrifugation, etc. have been described, large scale processing advantageously employs the process as a continuous one, wherein separation of the small particles from the liquid medium can be achieved using a settling tank, or the like, to avoid batch process limitations frequently encountered by centrifugation apparatus. Of course, if economies allow, a plurality of separating devices can be used, to take advantage of, e.g., the speed of centrifugation, and maintain a continuous process.

BRIEF DESCRIPTION OF THE DRAWING

The FIGURE illustrates the inventive process schematically, using 5 screens and a centrifuge as a separating device.

DETAILED DESCRIPTION OF THE INVENTION

The practice of the inventive process requires the use only of conventional apparatus, arranged in a unique, fluid communication pathway. Thus, the source of the desired biological agent or other preparation is introduced with the basic liquid supply, e.g.., plant water. In the case of biological agents derived from host insects, e.g., caterpillar, the whole caterpillar, together with an adequate water supply, is introduced to a homogenizer. The liquid homogenate is continuously passed to a first screen, e.g., a 100 mesh vibratory screen 102. If economies allow, these screens may be replaced with ultrafiltration membranes and appropriate filtration apparatus, a hollow fiber filter press, etc. All that is required of the screen or filter is that it allow smaller particles to pass in one direction, together with a liquid suspension, while retaining or redirecting larger particles separated therefrom. The small particle stream may ultimately be directed to a separator of some type such as a centrifuge, settling chamber, and the like. Any device capable of separating the small particles from the liquid in which they are entrained is sufficient for these purposes. The solid material recovered from the separator is treated to appropriate processing. If a centrifuge is employed, the recovered material may be extruded, or otherwise prepared, and packaged for ultimate use. Supernatant drawn from the centrifuge 104 may be directed to the system downstream of the first stream. The large particle stream is directed to an agitator 106, or similar mixing device, the water supply for which may be constituted, in whole or in part, by the water recovered from the subsequent separation stages. The only constraint on the liquid supply for the agitator is that the concentration of small particles therein be lower than the concentration of small particles in the surface water retained on the large particles separated off at screen 102.

As the large particles are distributed throughout the water supply and the agitator, the small particles will be distributed through the suspension. This suspension is directed to the second screen 108, of similar dimensions to screen 102, e.g., 100 mesh. At the screen, the small particles, together with water remaining, are removed and may be forwarded to some type of separation means, while the large particles are recovered separately. It will be noted that the large particles recovered after screen 108 will again carry a certain amount of surface water with them. The surface water or wetting water of the large particles separated off at screen 108 will have a substantially lower concentration of the desired small particles than those separated off after screen 102, demonstrating the effectiveness of the process. It should be further noted that where the large particle stream is the desired material, after passing through each successive screen, a higher degree of purity is obtained. The system can proceed through any number of screens, e.g., five or more, to further improve separation efficiency, where subsequent processing, and the economics of the process, require. Thus, the system can move from screen 108 to agitator 110, followed by screen 112, agitator 114 and screen 116.

At second and subsequent screens, the small particle/fluid stream recovered may be directed in one of three fashions. First, the stream may be directed to the separating means 122, wherein the small particles are separated off from the fluid, recovered and subsequently processed as desired. Second, the small particle/fluid stream may be directed to the agitator for the large particles separated off at any prior screen. This ensures that the concentration of the small particles in the fluid system of the agitator will be lower than the concentration of small particles in the wetting water on the surface of the large particles separated. Third, the small particle/fluid stream may be returned to the biological preparation step, stage 1, for further separation of the small particle fraction. The small particle/fluid stream may be divided into one or more streams, as desired, and employed in the above recirculation modes. Ultimately, of course, the filtrate obtained from the final screen or filter means must be directed to the separator means, in order to recover the smaller particle. Where recovery of the large particle only is desired, constant recycling of the small particle/fluid stream is appropriate.

In a preferred embodiment, separating means 122 includes a fine mesh screen 124 and a bag filter or similar filtering means 126, between the small particle stream and centrifuge 104. Enough supernatant is drawn off as waste from centrifuge 104 to balance fresh liquid supply at 120.

Where necessary for processing conditions, a wide variety of filters, sterilizers and the like, may be introduced in the fluid pathway, to ensure harmonious operation.

The process invention described above has been described with regard to specific means, as well as generic description. The specific apparatus to be employed is not restricted, and other apparatus capable of performing the identical or similar function is satisfactory. Thus, other filtering means, instead of screens, may be used, and a variety of separation means, such as settling chambers, centrifuges, and the like, may be employed in place of each other, or together. Alternatives will occur to those of ordinary skill in the art without the exercise of inventive faculty. The invention remains without limitation, save for those recited in the claims set forth below.

What is claimed is:

1. A continuous process for the separation of particles of at least two sizes from a preparation, comprising the sequential steps of:

A) preparing in a preparation means a liquid biological preparation comprising particles of at least two different sizes in a liquid medium, B) introducing said biological preparation to a first filter means which passes one said sized particle and said liquid while retaining said second sized particle, said second sized particles so retained bearing wetting liquid on their surface, in which wetting liquid is entrained a portion of said first sized particles, C) directing said first sized particles and liquid stream passed to at least one of said preparation means and a separator means in which separator means said first sized particle is separated off from said liquid, D) directing said retained particles to a liquid (i) having a concentration of said first sized particles lower than that of said wetting liquid and mixing said second sized particles therein, to form a suspension, E) directing said suspension to a second filter means which passes particles of said first size and said liquid while retaining particles of said second size, F) directing said passed particles of said first size and said liquid to at least one of said preparation means, said liquid (i) and a separator means, provided that in at least one of said steps (C) and (F) at least a portion of said stream is directed to a separator means wherein said particles of said first size are separated from said liquid, whereby said particles of said first and second size are separated.

2. The process of claim 1, wherein at least a portion of the liquid separated from said particles of said first size in said separating means is recycled to at least one of said preparation means, and said liquid (i).

3. The process of claim 1, wherein said steps (B) and (C) are repeated after step (F), at least once.

4. The process of claim 1, wherein steps (B)-(F) are repeated at least once.

5. The process of claim 1, wherein said liquid is water.

6. The process of claim 1, wherein said particles of said first size comprise inclusion bodies.

7. The process of claim 1, wherein additional liquid is added to said system to maintain the overall system at a constant concentration by addition of liquid to said liquid (i).

* * * * *